(12) United States Patent
Hashizume et al.

(10) Patent No.: US 10,830,636 B2
(45) Date of Patent: Nov. 10, 2020

(54) VARIATION MEASUREMENT DEVICE FOR PHYSICAL ACTIVITY AND DISPLAY METHOD OF VARIATION FOR PHYSICAL ACTIVITY

(71) Applicant: SHIMADZU CORPORATION, Kyoto (JP)

(72) Inventors: Nobuya Hashizume, Kyoto (JP); Shinichi Utsunomiya, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 199 days.

(21) Appl. No.: 15/882,378

(22) Filed: Jan. 29, 2018

(65) Prior Publication Data

US 2018/0224323 A1    Aug. 9, 2018

(30) Foreign Application Priority Data

Feb. 3, 2017  (JP) .................. 2017-018834

(51) Int. Cl.
| | |
|---|---|
| *G01G 19/415* | (2006.01) |
| *G01G 19/44* | (2006.01) |
| *G01G 23/37* | (2006.01) |
| *A61B 5/00* | (2006.01) |
| *G01G 19/414* | (2006.01) |
| *A61B 5/11* | (2006.01) |

(52) U.S. Cl.
CPC ......... *G01G 23/3721* (2013.01); *A61B 5/742* (2013.01); *G01G 19/415* (2013.01); *G01G 19/4146* (2013.01); *G01G 19/44* (2013.01); *A61B 5/1118* (2013.01)

(58) Field of Classification Search
CPC .......... G01G 23/3723; G01G 19/4146; G01G 19/415; G01G 19/44; A61B 5/742; A61B 5/1118
See application file for complete search history.

(56) References Cited

U.S. PATENT DOCUMENTS

| | | | | |
|---|---|---|---|---|
| 4,301,879 A | * | 11/1981 | Dubow .................. | G01G 19/44 177/178 |
| 4,423,792 A | * | 1/1984 | Cowan .................. | G01G 19/62 177/1 |
| 4,487,278 A | * | 12/1984 | Rosenthal ............ | G01G 19/414 177/1 |

(Continued)

FOREIGN PATENT DOCUMENTS

| | | |
|---|---|---|
| JP | 2016-176797 | 10/1918 |
| JP | H11-332845 | 12/1999 |

(Continued)

OTHER PUBLICATIONS

EP 18000073.9, European Search Report dated Jun. 12, 2018, 8 pages.

(Continued)

*Primary Examiner* — Randy W Gibson
(74) *Attorney, Agent, or Firm* — Andrew F. Young, Esq.; Lackenbach Siegel, LLP (57) ABSTRACT

A variation measurement device for a physical activity includes a display element that displays a variation amount of a weight data from a benchmark of the weight data, which varies depending on the physical activity of the measurement subject.

10 Claims, 6 Drawing Sheets

(56) References Cited

U.S. PATENT DOCUMENTS

| | | | |
|---|---|---|---|
| 6,354,996 B1 * | 3/2002 | Drinan | A61B 5/0537 128/903 |
| 6,516,221 B1 * | 2/2003 | Hirouchi | A61B 5/0537 600/547 |
| 6,679,854 B2 * | 1/2004 | Honda | A61B 5/0537 600/587 |
| 6,734,856 B2 * | 5/2004 | Ishikawa | A61B 5/0537 345/440 |
| 6,766,272 B2 * | 7/2004 | Serita | A61B 5/0537 702/155 |
| 7,994,439 B2 * | 8/2011 | Daniels | G01G 19/4146 177/25.13 |
| 8,475,367 B1 * | 7/2013 | Yuen | G06F 19/3418 600/300 |
| 8,541,700 B2 * | 9/2013 | Sato | G01G 23/3728 177/25.11 |
| 2002/0087102 A1 | 4/2002 | Honda et al. | |
| 2010/0130831 A1 | 5/2010 | Sato et al. | |
| 2011/0106553 A1 | 5/2011 | Sato et al. | |
| 2012/0330683 A1 * | 12/2012 | Ledwidge | A61B 5/0002 705/3 |
| 2014/0224552 A1 | 8/2014 | Shimizu et al. | |
| 2016/0120461 A1 | 5/2016 | Kato et al. | |

FOREIGN PATENT DOCUMENTS

| | | |
|---|---|---|
| JP | A2001190514 | 7/2001 |
| JP | 2010-260327 | 11/2010 |
| JP | 2011-191233 | 9/2011 |
| WO | WO 2008/023978 | 2/2008 |

OTHER PUBLICATIONS

EP 18000073.Search Report dated Apr. 17, 2020, 7 pages—English.
EP 18 000 073.9, Response to European Search Report (ESR) dated Feb. 6, 2019, 17 pages—English.
2017-018834, Notice of Reasons for Refusal, dated Mar. 9, 2020, 4 pages—Japanese, 4 pages—English.

* cited by examiner

```
Per one minute
            -0.86 g
```

*FIG. 5*

```
Per 10 minutes
            −8.64 g
```

*FIG. 6*

Time needed for
100g weight decrease

1 HOUR and 56 MINUTES

VARIATION MEASUREMENT DEVICE FOR PHYSICAL ACTIVITY AND DISPLAY METHOD OF VARIATION FOR PHYSICAL ACTIVITY

CROSS REFERENCE TO RELATED APPLICATIONS

This application relates to and claims priority from JP Ser. No.: 2017-018834 filed Feb. 3, 2017, the entire contents of which are incorporated herein by reference.

FIGURE SELECTED FOR PUBLICATION

Figure 1A:
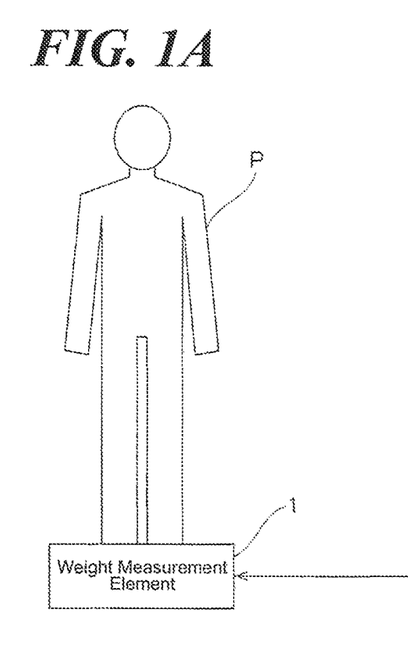
FIGS. 1A, 1B are views illustrating a structure of a variation measurement device for a physical activity according to the aspect of the Embodiment of the present invention.
Figure 1B:
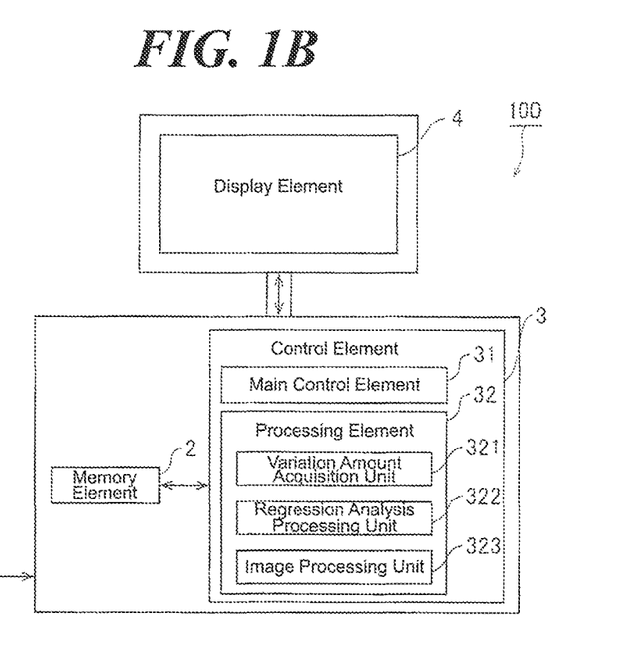

FIGS. 1A, 1B

BACKGROUND OF THE INVENTION

Field of the Invention

The present invention relates to a measurement device of a variation due to a physical activity and a display method of the variation due to the physical activity, and particularly, relates to the measurement device of a weight variation of a measurement subject due to the physical activity and the display method of the variation due to the physical activity.

Description of the Related Art

Conventionally, a variation measurement device that comprises a display capable of displaying the weight variation of the measurement subject due to the physical activity is known. Such the variation measurement device that measures the variation due to the physical activity is disclosed in e.g. the Patent Document JPH11-332845 A1.

The Patent Document JPH11-332845 A1 discloses the health management guideline advice device (measurement device of a variation due to a physical activity) having a health management data acquisition means that acquires the health management benchmark including a body weight and an amount of body fat and so forth, an acquiring data acquisition means that acquires the data when acquiring the health management benchmark, a history data calculation means that acquires a history data of the health management data based on the health management benchmark and the acquiring data, and a display element that displays the data such as the health management benchmark and so forth. In addition, the display element displays the time-course variation of the health management benchmark using the letter data, such as numbers and graphs. Specifically, the variation amount due to the difference between the body-weight when the diet starts and the past or present body-weight other than when the diet starts can be converted to the monthly variation to be displayed, and the time-course variation of the average body-weight every month from when the diet starts until when the goal date passes can be displayed as the line-graph. In addition, the measurement unit of the body-weight is 0.1 Kg (100 g). In addition, the timing of the body-weight measurement is not clear, but supposedly, the measurement frequency is one time per day due to the expressions such as an amount of consumption calorie per day, an energy amount to be consumed by an exercise per day and so forth.

Now, the body-weight (weight) of the measurement subject varies depending on a variety of factors including meals, drinks, sweating, elimination, exercise and daily activity, and insensitive sweating during resting state and so forth.

Nevertheless, the health management guideline advice device (measurement device of a variation due to a physical activity) according to the Patent Document WH11-332845 A1 measures (displays) the weight variation amount based on the relatively long time-interval (per month and for several months) and using a relatively large unit (100 g). The body-weight varies depending on a variety factors as set forth above, so that even when the body-weight is measured at the beginning of the day or the end thereof and the weight variation for several days to several months is displayed, the weight variation due to one physical activity (e.g., running and so forth as a physical exercise) that is practiced in a relatively short time period such as an hour unit or a minute unit during daytime can be hardly realized in direct. In addition, given the body-weight is measured before and after one physical activity that is practiced in a short period of time such as 10 minutes or an hour and so forth, the body-weight measurement unit is 100 g, so that it can be hard to measure (display) accurately such relatively small weight variation, due to one predetermined physical activity such as an exercise and so forth. Therefore, the health management guideline advice device (measurement device of a variation due to a physical activity) according to the Patent Document JPH11-332845 A1 is hardly applied to measures (displays) the weight variation amount in the short time-interval and per small unit corresponding to the one predetermined physical activity. As a result, it is problematic that the weight variation due to the one predetermined physical activity that is practiced in a relatively short period of time such as an hour unit or a minute unit is hardly realized,

ASPECTS AND SUMMARY OF THE INVENTION

According to one aspect of the present invention, there is presented a variation measurement device for a physical activity includes a display element that displays a variation amount of a weight data from a benchmark of the weight data, which varies depending on the physical activity of the measurement subject.

The present invention is proposed to solve the problems set forth above and one of the purposes of the present invention is to provide a measurement device for a variation due to a physical activity, which measures the weight variation relative to one predetermined physical activity that is practiced in a relatively short period of time such as per hour unit or per minute unit.

To achieve the above purpose, according to the aspect of the present Embodiment 1 of the present invention, a measurement device for a physical activity (variation measurement device for physical activity) comprises; a weight data memory element that stores each weight of a measurement subject, which is measured multiple times by a weight measurement element between a beginning of a predetermined physical activity of the measurement subject and an end thereof; as weight data in association with each measurement time, a control element that acquires the weight data variation amounts that are differences between weight data as a benchmark that is specified among a plurality of weight data that are stored in the weight data memory element and the weight data other than the specified benchmark weight data, a display element that displays a variation amount of the weight data from the benchmark of the weight data, which varies depending on the physical activity of the measurement subject.

With regard to the variation measurement device for physical activity according to the first aspect of the present invention, as set forth above, the display element displays a variation amount from the benchmark of the weight data of the measurement subject, which are measured multiple times between the beginning of the one predetermined physical activity of the measurement subject and the end thereof. Therefore, the variation amount is acquired (displayed) based on the measured weight data, so that the variation amount of a relatively small weight that varies during one physical activity (e.g., running and so forth) that is performed in a relatively short period of time such as in an hour or minutes unit can be acquired (displayed). For example, when the variation amount is acquired (displayed) based on the weight data that are measured by a small unit less than 100 g (e.g., 1 g or 10 g), the relatively small weight variation that takes place between the beginning of the one predetermined physical activity of the measurement subject and the end thereof can be measured. As a result, the weight variation during the one predetermined physical activity can be figured out. In addition, the variation amount between the weight data as the benchmark and the weight data other than the benchmark is displayed, so that such display can facilitate to compare to the variation amount of the weight data of the (same or different kind of physical activity at the different time. Specifically, given the measurement condition of the measurement subject, e.g., different wears, a meal-intake or not before beginning of the physical activity, and so forth, is different, and when the absolute value of the weight data is plotted and displayed as-is on the same graph while plotting the weights on a graph, a plurality of weights having the different height (y-coordinate) of the starting point (the weight at the beginning) on the graph is displayed in parallel. Accordingly, it is difficult to realize the difference with one another. On the other hand, when the variation amount is displayed according to the aspect of the present invention, the heights (y-coordinate) of the starting point are the same, so that such display facilitates to compare the variation amounts and so forth, of a plurality of the weight data measured under the different condition relative to the measurement subject. As a result, the difference between the variation amount of a plurality of the weight data of the physical activity (of the same or the different kind) at the other measurement time when the condition of the measurement subject is different with one another can be easily realized.

In addition, according to the aspect of the present invention, the physical activity is a broad concept including the resting state, the daily activity that is the state consuming more energy than the resting state, and an exercise that is performed for the purpose of maintenance and improvement of the body strength in a planned and intended manner. In addition, the one predetermined physical activity denotes that one kind of the physical activity among the resting state, the daily activity, and a physical exercise is performed as a series of activities (for example, a walk-moving, a cleaning and so forth in the daily activity, a running as a physical exercise, a swimming, or a circuit training such as 10 times push-ups following 10 times sit-ups and so forth). Specifically, "one" is collectively the term (between the beginning and the end of the activity) in which a physical activity (physical exercise and so forth) is performed as a series of the activities without considering a temporary suspension of the activity due to the weight measurement of the measurement subject.

With regard to the variation measurement device for physical activity according to one aspect set forth above, it is preferable that the display element displays the variation amount of the weight based on the weights that are measured as one predetermined physical activity between the beginning and the end of the one physical exercise. Therefore, such aspect can facilitate to realize a weight decrease due to one specific physical exercise that is performed in units of hour or minute.

With regard to the variation measurement device for physical activity according to one aspect set forth above, it is preferable that the control element fits the variation amounts from the benchmark to an approximate straight line or an approximate curve by a regression analysis, and in addition, displays the graph denoting the time-course variation of the plurality of the weight data based on the approximate straight line or the approximate curve acquired by the fitting on the display element. Such aspect can facilitate to realize the entire trend of the weight variation (variation rate) from the gradient of the graph based on the approximate straight line or the approximate curve.

With regard to the variation measurement device for physical activity according to one aspect set forth above, it is preferable that the control element estimates the time when the weight data reach the expected variation amount based on the approximate straight line or the approximate curve acquired by the fitting, and displays such time on the display element. Such aspect can facilitate to estimate and display the time when the weight data reach the expected variation amount based on the acquired approximate straight line or the acquired approximate curve given the same activity goes on.

With regard to the variation measurement device for physical activity according to one aspect set forth above, it is preferable that the control element displays the variation amount that is converted to per unit time based on the approximate straight line or the approximate curve acquired by the fitting on the display element. According to such aspect, it can be accurately displayed how much the weight data varies per unit time.

To achieve the above purpose, a variation display method for a physical activity according to the second aspect of the present invention comprises; the step of measuring a weight of a measurement subject multiple times between the beginning of the one predetermined physical activity of the measurement subject and an end thereof; the step of storing each weight that is measured multiple times as weight data in association with each measurement time; the step of acquiring the weight data variation amount from a difference between weight data as a benchmark that is specified among the weight data that are stored therein; and the step of displaying a variation amount of acquired weight data from the benchmark of the weight data of the measurement subject, which varies depending on the one predetermined physical activity.

With regard to the variation display method for physical activity according to the second aspect of the present invention, as set forth above; the step of displaying, a variation amount from a benchmark of weight data of a measurement subject, which is measured multiple times between a beginning of the one predetermined physical activity of the measurement subject and an end thereof. Therefore, the variation amount is acquired (displayed) based on the measured weight data, so that the variation amount of a relatively small weight that varies during, one physical activity (e.g., running and so forth) that is performed in a relatively short period of time such as in an hour or minutes unit can be acquired (displayed). For example, when the variation amount is acquired (displayed) based on the weight data that are measured by a small unit less than 100 g (e.g., log), the relatively small weight variation that takes place between the beginning of the one predetermined physical activity and the end thereof can be measured. As a result, the weight variation during the one predetermined physical activity can be figured out. In addition, the variation amount between the weight data AS the benchmark and the other weight data are displayed, so that such display can facilitate to compare to the variation amount of the weight data of the (same or different kind of) physical activity at the different time. Specifically, given the measurement condition of the measurement subject, e.g., different wears, a meal-intake or not before beginning of the physical activity, and so forth, is different, and when the absolute value of the weight data is plotted and displayed as-is on the same graph while plotting the weights on a graph, a plurality of weights having the different height (y-coordinate) of the starting point (the weight at the beginning) on the graph is displayed in parallel. Accordingly, it is difficult to realize the difference with one another. On the other hand, when the variation amount is displayed according to the aspect of the present invention, the heights (y-coordinate) of the starting point are the same, so that such display facilitates to compare the variation amounts and so forth of a plurality of the weight data measured under the different condition relative to the measurement subject. As a result, the difference between the variation amount of a plurality of the weight data of the physical activity (of the same or the different kind) at the other measurement time when the condition of the measurement subject is different with one another can be easily realized.

With regard to the variation display method for physical activity according to the second aspect as set forth above, it is preferable that the step that displays the variation amount comprises the step of displaying the variation amount of the weight based on the weight that is measured as one predetermined physical activity between the beginning and the end of the one physical exercise. Therefore, such aspect can facilitate to realize a weight decrease due to one specific physical exercise that is performed in a unit of hour or minute.

The above and other aspects, features and advantages of the present invention, will become apparent from the following description read in conjunction with the accompanying drawings, in which like reference numerals designate the same elements.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

As used, herein, and as will be understood by one of skill in the computer engineering and computer science arts, a 'computer-type system' includes an input device for receiving data, an output device for outputting data in tangible form (e.g. data transmission, data display, printing or displaying on a computer screen, data storing, data manipulation, data calculation, etc.), a memory for storing data as well as computer code, and a processor (of any kind) for executing computer code wherein said computer code resident in said memory (permanent or transitory) will physically cause said microprocessor to read-in data via said input device, process said data within said processor(s) and output said processed data via said output device.

Preferred Aspect of the Embodiment

The inventor sets forth specific Embodiments of the present invention based on the following FIGs.

Embodiment

First, referring to FIG. 1A, FIG. 1B the inventor sets forth the structure of the variation measurement device 100 for a physical activity according to the aspect of the Embodiment 1 of the present invention. Referring to FIG. 1A, FIG. 1B, the variation measurement device 100 for the physical activity according to the aspect of the Embodiment comprises a weight measurement element 1, a memory element 2, a control element 3 and a display element 4. In addition, the weight measurement element 1 and the display element 4 are connected to the memory element 2 and the control element 3 respectively.

The weight measurement element 1 measures a weight of a measurement subject multiple times in a unit of 10 g between a beginning of the one predetermined physical activity of the measurement subject and an end thereof in addition, the measured weight is stored in the memory element 2 (set forth later) and output to the control element 3 (set forth later) in association with the measurement time every measurement. The inventor sets forth later the specific measurement procedure in detail.

Now, according to the aspect of the present Embodiment, the memory element 2 stores each weight of the measurement subject P, which is measured multiple times by the weight measurement element 1 capable of measuring in the unit of 10 g between the beginning of the one predetermined physical activity of the measurement subject P and an end thereof, as weight data in association with a measurement time. In addition, the memory element 2 stores a variety of programs that a main control element 31 and a processing element 32 execute. In addition, the memory element 2 comprises a memory device such as e.g., a HDD (hard disk drive). Further, the operation element 2 is an example of a "velocity operation element" in the claims.

The control element 3 that comprises such as a data processing unit such as a PC (personal computer) and so forth exchanges the signals (data) with the weight measurement element 1, the memory element 2 and the display element 4. The control element 3 comprises the main control element 31 such as CPU (central processing unit) and so forth, and a processing element 32 having a variation amount acquisition unit 321, a regression analysis processing unit 322 and a processing element 32. In addition, the arrow in FIG. denotes the exchange of the signal (data).

The main control element 31 executes the control program that the memory element 2 stores, so that the PC can be operative as the control element 3 of the variation measurement device 100 for physical activity.

In addition, according to the aspect of the present Embodiment, the variation amount acquisition unit 321 that the control element 3 comprises, acquires the variation amount of the weight data from the difference between the weight data as a benchmark and the other weight data other than the benchmark. In addition, the variation amount acquisition unit 321 outputs the acquired variation amount of the weight data to the regression analysis unit 322. In addition, the benchmark is the data of the weights that are measured at the beginning. The inventor sets forth about the weight data acquisition later in detail.

In addition, according to the aspect of the present Embodiment, the regression analysis unit 322 that the control element 3 comprises acquires the approximate straight line by fitting the variation amount from the benchmark to the approximate straight line using the regression analysis. In addition, the regression analysis unit 322 acquires the variation graph along the time-course of a plurality of the weight data based on the approximate straight line acquired by the fitting. In addition, the regression analysis unit 322 estimates the time when the weight data reaches the expected variation amount based on the approximate straight line acquired by the fitting. In addition, the regression analysis unit 322 acquires the variation amount of the weight data that is converted to per unit time based on the approximate straight line acquired by the fitting.

The data that are acquired by the regression analysis unit 322 are output to the image processing unit 323. Specifically, the regression analysis unit 322 executes a regression analysis relative to the weight data in association with each measurement time acquired by the variation amount acquisition unit 321, and outputs the signal of the data based on the approximate straight line subjected to fitting to the image processing unit 323. The inventor sets forth later the specific measurement procedure in detail.

In addition, according to the aspect of the present Embodiment, the image processing unit 323 that the control element 3 comprises displays the variation amount of the weight data of the measurement subject from the benchmark (weight data), which varies depending on the one predetermined physical activity that is acquired by the variation amount acquisition unit 321 that the control element 3 comprises. In addition, the image processing unit 323 displays the variation graph along the time-course of a plurality of the weight data based on the approximate straight line acquired by the regression analysis unit 322 on the display element 4. In addition, the image processing unit 323 displays the time until the weight data, which is estimated based on the approximate straight line acquired by the fitting using regression analysis unit 322, reach the expected variation amount on the display element 4. In addition, the image processing unit 323 displays the variation amount of the weight data converted per time unit, which is acquired based on the approximate straight line acquired by the fitting using the regression analysis unit 322, on the display element 4.

Specifically, the image processing unit 323 processes the data relative to the variation amount of the weight of the measurement subject from the benchmark, the data relative to the variation graph along the time-course of the plurality of the weight data, the data relative to the time passed until the weight data reach the expected variation amount, and the data relative to the variation amount of the weight data converted to per time unit, and so forth, and outputs to the display element 4 as the image data signal.

In addition, according to the aspect of the present Embodiment, the display element 4 displays the variation amount of the weight data of the measurement subject from the benchmark, which varies depending on the one predetermined physical activity and are acquired by the variation amount acquisition unit 321 that the control element 3 comprises, based on the signal (data) output from the image processing unit 323. In addition, the display element 4 displays the image data (letter data and a graph and so forth) of the variation graph along the time-course of the plurality of the weight data, the data relative to the time passed until the weight data reach the expected variation amount, and the data relative to the variation amount of the weight data converted to per time unit, and so forth, which are acquired based on the approximate straight line that is subjected to the fitting and acquired by the regression analysis unit 322 based on the signal (data) output from the image processing unit 323.

(Weight Measurement and Regression Analysis)

Next, referring to FIG. 2-FIG. 6, the inventor sets forth the method (a variation display method of a physical activity) of executing a weight measurement and a regression analysis of the variation amount of the weight data and displaying the result thereof on the display 4 using the variation measurement device 100 for physical activity along the procedure.

For example, the variation measurement device 100 for physical activity measures the weight data variation amount from the beginning of a work (physical exercise) of a measurement subject P as the one predetermined physical activity to the end thereof, and executes a regression analysis relative to the variation amount of the weight data, and acquires and displays a variety of values. In addition, the work of the measurement subject is an example of a "one predetermined physical activity" in the claims.

Firstly, the weight measurement element 1 measures the weight of the measurement subject P, who gets on the table (scale) of the weight measurement element 1, adequate-multiple times per 10 g unit (e.g., every 15 minutes) between the beginning and the work to the end thereof. Secondary, each weight that is measured multiple times is stored in the memory element 2 as weight data in association with a measurement time. Thirdly, the variation amount acquisition unit 321 acquires the weight data variation amount from the difference between the benchmark weight data (benchmark) that is specified among the weight data that are stored in the memory element and the weight data other than the benchmark weight data.

Fourthly, the regression analysis unit 322 acquires the approximate straight line subjected the fitting of the weight data. In addition, the time passed until the weight data reach the expected variation amount based on the approximate straight line acquired by the regression analysis unit 322, and the variation amount of the weight data that is converted to per unit hour, and so forth are acquired. Then the display element 4 displays the measurement results including the variation amount of the weight data from the benchmark of the measurement subject. Which varies depending on the one physical activity and the processing results.

Figure 2:
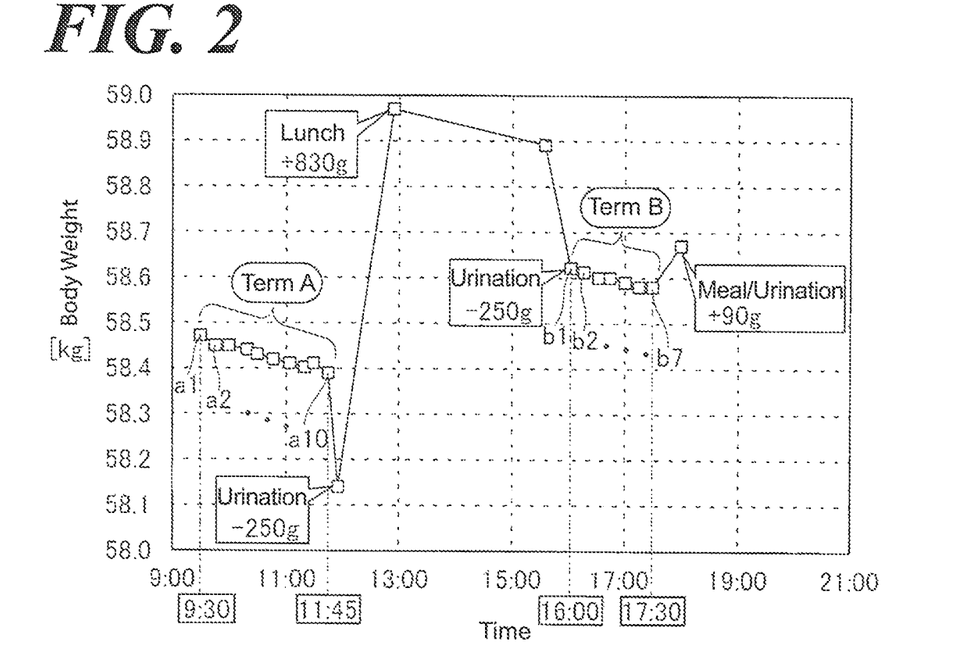
FIG. 2 is a graph illustrating a time-course variation of a weight due to a physical activity including two working terms relative to one measurement subject.

Now, referring to FIG. 2, the inventor sets forth one example of the actual measured data. FIG. 2 is the graph illustrating the measurement result of a measurement subject P along the time axis. The vertical axis denotes the absolute weight (Kg) of the measurement subject P and the horizontal axis denotes the measurement time. Here, the weight variation of the measurement subject P is measured when working (doing a physical exercise). Specifically, the measurement subject P is working (doing the physical exercise) in 2 measurement terms of the term A and the term B. In addition, a urination or a meal-intake takes place between 2 measurement terms.

The weight of the measurement subject P is measured one time every approximately 15 minutes and the total 10 times in the term A between around 9:30 and around 11:45, and the weight data a1, a2, . . . , a10 are stored in the memory element 2. The weight of the measurement subject is a1=58.47 Kg at the first measurement of the weight (benchmark) and the last (10th) measurement weight thereof is a10=58.39 kg. Therefore, it is realized that the weight variation amount in-between around 135 minutes is approximately 80 g. Specifically, relative to the one predetermined physical activity as the work (physical exercise), the weight of the total approximately 80 g decreases between the beginning (a1) of the measurement and the end of the measurement (a10) and it is realized that approximately 5.9 g, as a simple average, decrease (variation) of the weight per 10 minutes takes place.

And 250 g of the weight of the measurement subject P decreases due to the urination and 850 g thereof increases due to a lunch meal following the term A. In addition, after the weight decreases slowly and gradually due to a physical activity such as walking and an insensitive sweating and so forth following the lunch meal, 250 g of the weight decreases due to the urination again.

Then, the weight of the measurement subject P is measured a total of 7 times every approximately 15 minutes in the term B between around 16:00 and around 17:30, and the weight data b1, b2, . . . , b7 are stored in the memory element 2. The weight of the measurement subject is b1=58.62 Kg at the first measurement of the weight (benchmark) and the last (7th) measurement weight thereof is b7=58.58 kg. Therefore, it is realized that the weight variation amount in-between around 90 minutes is approximately 40 g. Specifically, relative to the one predetermined physical activity as the work (physical exercise), the weight of the total approximately 40 g decreases between the beginning (b1) of the measurement and the end of the measurement (b7) and it is realized that approximately 4.44 g, as a simple average, decrease (variation) of the weight per 10 minutes takes place.

Figure 3:
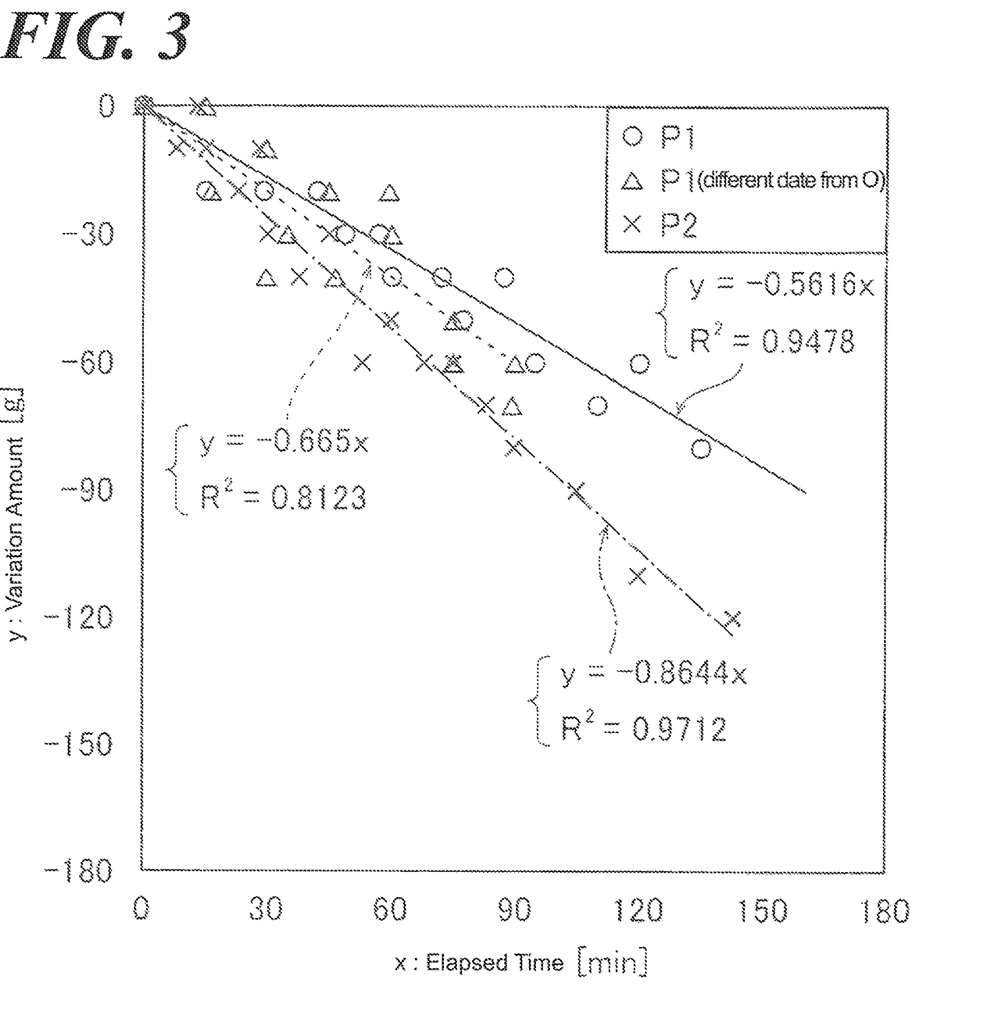
FIG. 3 is a graph illustrating a plurality of approximate straight lines when the variation amount of the weight data is subjected to the regression analysis.
Figure 4:
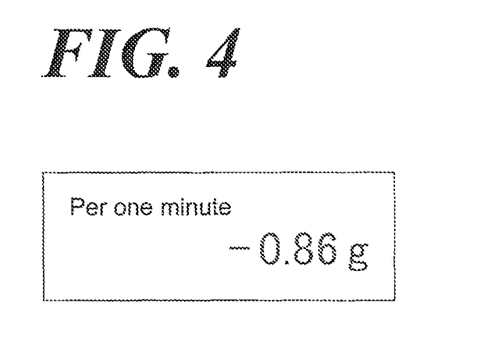
FIG. 4 is a schematic view illustrating one display example of the variation amount of the weight data.
Figure 5:
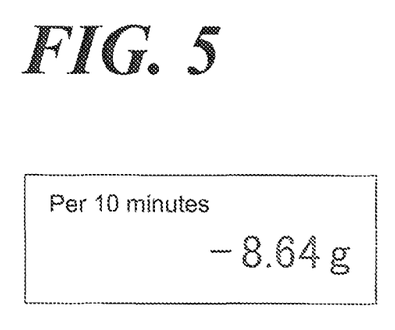
FIG. 5 is a schematic view illustrating one display example of the variation amount of the weight data per 10 minutes.
Figure 6:
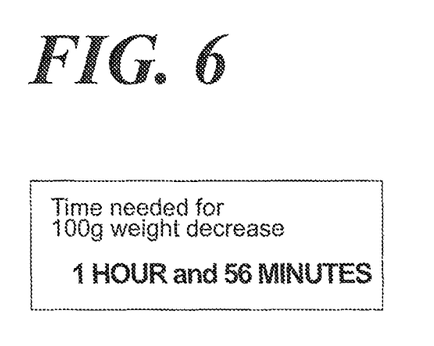
FIG. 6 is a schematic view illustrating one display example the time passed until the 100 g variation takes place.

Next, referring to FIG. 3, the inventor sets forth the regression analysis relative to the variation amount of the weight data that are acquired as set forth above and an Embodiment to acquire a variety of measurement results. Referring to FIG. 3, the display element 4 displays the approximate straight line of the regression analysis results relative the variation amount of the weight data and the mathematical formulae that provide such approximate straight line. The solid line plotted by circles is based on the variation amount of the weight data, and is the approximate straight line illustrating the weight variation when the measurement subject P1 works (physical exercise). The vertical axis is the variation amount (g) of the weight and the horizontal axis is an elapsed-time (min). The dotted line plotted by triangles is based on the variation amount of the weight data, and is the approximate straight line illustrating the weight variation when the measurement subject P1 works (exercise) the other day than the date denoted by the sold line. The dashed-dotted line plotted by crosses is based on the variation amount of the weight data, and is the approximate straight line illustrating the weight variation when the measurement subject P2 that is different from the measurement subject P1 works (physical exercise).

In addition, R2 is a characteristic (determination coefficient) that denotes a ratio of the regression variation based on the total variation in the vertical axis direction. In addition, with regard to the mathematical formula, the mathematical formula in FIG. 3 can be displayed as-is, or without displaying the mathematical formula per se, the variation amount per hour as set forth later following the conversion to the variation amount per hour based on the portion corresponding to the straight-line gradient (e.g., value −0.5616 of the graph indicated by circles) can be displayed.

In addition, the display element 4 displays the time passed until the weight data reaches the expected variation amount based on the approximate straight line, and the variation amount of the weight data that is converted to per unit hour, in addition to the graph of the approximate straight line. Specifically, when the measurement result of the measurement subject P2 is displayed, the display element 4 displays that approximately 0.86 g (referring to FIG. 4) of the weight decreases per minute and approximately 8.64 g (referring to FIG. 5) of the weight per 10 minutes decreases relative to the measured one predetermined physical activity (work (physical exercise)) based on that the variation (gradient) value of the acquired weight variation is −0.864. In addition, the display element 4 displays that the approximate physical exercise time is needed to reach the expected weight based on that the variation (gradient) value of the acquired weight variation is −0.864 given the measurement subject P2 keeps the same physical activity (work (physical exercise)). For example, when the user wants to display the goal time required to provide 100 g of the variation, the display element 4 displays that it is approximately one hour and 56 minutes (approximately 116 minutes, referring to FIG. 6) based on the calculation result by 100/0.864.

In addition, the display element 4 may display the graph of the above approximate straight line, the variation per hour, the physical exercise amount needed to achieve the expected variation amount and so forth individually or at the same time. In addition, the display element 4 compares the present (most recent) measurement result with the past measurement, and may display each measurement result at the same time.

In addition, the example in which the physical activity in the relatively short period of time is set forth, but when the measurement takes a long time, the measurement subject P may take a drink in the middle of the one predetermined physical activity whereby the weight variation may take place. In such case, the control element 3 may execute the regression analysis on each weight data before and after the weight varies largely due to a water-intake and so forth.

In addition, activity according to the aspect of the present Embodiment, the variation measurement device 100 for a physical activity realizes the overall trend relative to the weight variation amount and a variation based on the approximate straight line acquired by the regression analysis. Therefore, the measurement subject P per se understands quantitatively that the metabolic amount (a weight variation amount and a variation) is different depending on the content of the work (physical exercise) and each individual by comparing the metabolic amount (weight, variation amount and variation) due to the own physical activity with another metabolic amount due to the own another physical activity, or the metabolic amount between the own physical activity and the other physical activity.

In addition, comparing to the consumption calorie display, the own weight variation of the measurement subject P is displayed, so that the measurement subject P per se can more practically realize the effect of the physical exercise. Further, comparing to the weight variation of the other date, the measurement subject P can realize the own variation of the metabolic amount (e.g., the increase of the metabolic amount along the increase of the muscle mass, the increase of strength of the physical exercise and so forth).

In addition, the measurement subject P uses to understand, realize and evaluate the own physical exercise amount and the effect thereof, and in addition, a trainer who is in charge of managing and guiding the measurement subject P can use to make a benchmark.

In addition, according to the aspect of the present Embodiment, the variation measurement device 100 for the physical activity the measurement subject P uses to realize the metabolic amount (the weight variation amount and the variation) due to the own physical activity, and in addition, a medical doctor and a caregiver can use to manage the health condition of the patient (measurement subject P). Specifically, it is known that the decrease of the muscle mass and narrowing of movable scope of the muscle take place as a sign at the beginning of a dementia and a motor disorder. For example, the weight variation amount of the same predetermined physical activity decreases, so that the sign at the beginning of a dementia and a motor disorder can be adequately realized. Therefore, for example, the weight variation amount (variation rate) due to the resting state and the walk (i.e., one example of the daily activity and the physical exercise) as a physical activity is acquired periodically, so that the variation of the metabolic amount in conjunction with the muscle mass of the patient (measurement subject P) and so forth can be realized and the benchmark to estimate the health condition of the patient (measurement subject P) can be obtained.

In addition, the weight variation due to the insensitive sweating is obtained when the patient (measurement subject P) is in the resting state, so that the water management for the patient (measurement subject P) can be adequately carried out. Specifically, a decrease amount of water of the patient (measurement subject P) is estimated using the weight variation amount, so that an amount of water that must be administered to the patient (measurement subject) through such as an intravenous drip can be realized (determined). In addition, for example, it is known that the water content of the body increases due to a heart failure (cardiac arrest). Accordingly, the water management can be applied to find out the sign of the disorder (heart failure and so forth) of the patient (measurement subject P).

In addition, according to the aspect of the present Embodiment, the variation measurement device 100 for the physical activity can be applied to evaluate the effect of the health food and so forth by understanding the change of the metabolic amount (weight variation amount and variation rate) by the weight variation amount due to an intake of health foods and so forth (e.g., foods that so-called accelerate a fat burning and increase sweating) relative to the metabolism.

(Effect According to the Aspect of the Embodiment)

The following effect can be obtained according to the aspect of the present Embodiment.

According to the aspect of the present Embodiment, as set forth above, the display element 4 displays the variation amount of the weight data of the measurement subject P, which are measured multiple times between the beginning and the end of the one physical activity (work (physical exercise) and so forth), from the benchmark. Therefore, the variation amount is acquired (displayed) 10 g in the unit based on the measured weight data, so that the variation amount of a relatively small weight that varies during one physical activity (work (physical exercise) and so forth), which is performed in a relatively short period of time such as in an hour or minutes unit, can be acquired (displayed). As a result, the weight variation during the one predetermined physical activity can be figured out. In addition, the variation amount between the weight data at the benchmark and the other weight data is displayed, so that such display can facilitate to compare to the variation amount of the weight data of the (same or different kind of) physical activity at the different time. Specifically, given the measurement condition of the measurement subject, e.g., different wears, a meal-intake or not before beginning of the physical activity, and so forth, is different, and when the absolute value of the weight data is plotted and displayed as-is on the same graph while plotting the weights on a graph, a plurality of weights having the different height (y-coordinate) of the starting point (the weight at the beginning) on the graph is displayed in parallel. Accordingly, it is difficult to realize the difference with one another. Whereas, when the variation amount is displayed according to the aspect of the present Embodiment, the heights of the starting point are the same, so that such display facilitates to compare the variation amounts and so forth of a plurality of the weight data measured under the different condition relative to the measurement subject. As a result, the difference between the variation amount of a plurality of the weight data of the physical activity (of the same or the different kind) at the other measurement time when the condition of the measurement subject is different with one another can be easily realized.

In addition, the display element 4 is the display element 4 that displays the variation amount of the weight based on the weight that is measured as one predetermined physical activity between the beginning and the end of the one physical exercise. Therefore, such aspect can facilitate to realize a weight, decrease due to the one specific physical exercise that is performed in units of hour or minute.

In addition, according to the aspect of the present Embodiment, as set forth above, the control element 3 (the regression analysis unit 322 and the image processing unit 323) fits the variation amounts from the benchmark to an approximate straight line by a regression analysis, and in addition, displays the graph denoting the time-course variation of the plurality of the weight data based on the approximate straight line acquired by the fitting on the display element 4. Such aspect can facilitate to realize the entire trend of the weight variation rate (rate of variation) from the gradient of the graph based on the approximate straight curve.

In addition, according to the aspect of the present Embodiment, as set forth above, the control element 3 (the regression analysis unit 322 and the image processing unit 323) estimates the time when the weight data reaches the expected variation amount based on the approximate straight line acquired by the fitting, and displays such time on the display element 4. Therefore, such aspect can facilitate to estimate and display the time when the weight data reaches the expected variation amount based on the acquired approximate straight given the same activity goes on.

In addition, according to the aspect of the present Embodiment, as set forth above, the control element 3 (the regression analysis unit 322 and the image processing unit 323) displays the variation amount of the weight data, which is converted to per unit time, on the display element 4 based on the approximate straight line acquired by the fitting. According to such aspect, it can be accurately displayed how much the weight data varies per unit time.

Alternative Embodiment

In addition, the aspects of the Embodiments disclosed at this time are examples and not limited thereto in any points. The scope of the present invention is specified in the claims but not in the above description of the aspect of the Embodiments and all alternative (alternative examples) are included in the scope of the claims and equivalents thereof.

For example, according to the aspect of the Embodiments set forth above, the example, in which the variation amount of the weight data is measured relative to the measurement subject who implement a work (a physical exercise), but the present invention is not limited thereto. According to the aspect of the present invention, the variation measurement device for a physical activity, which is installed in e.g., a sports gym and so forth, may measure a metabolic amount (a variation rate or a variation amount of weight) due to the physical exercise of the measurement subject. Specifically, for example, the weight measurement element measures the weight of the measurement subject in the unit of 10 g so that the measurement subject. P can realize how much about the own weight varies when taking on the treadmill and the exercise bike and so forth for 30 minutes physical exercise (physical exercise as a physical activity). The measurement subject measures the own weight using the weight measurement element prior to beginning of the physical exercise. Then, the measurement subject moves to the variation measurement device for physical activity, which is equipped near by the treadmill and the exercise bike and so forth, to measure the own weight every physical exercise for approximately 10 minutes. Accordingly, the weight measurement element 1 carries out the total four weight measurements including one prior to beginning of running and so forth, twice every 10 minutes in-between runnings and so forth, and one at the end of the running and so forth. Each weight is stored in the memory element in association with a measurement time. In addition, the physical exercise using the treadmill, or the exercise bike is an example of "one physical exercise" in the claims, At this time, the variation amount acquisition element acquires the difference between the first measured weight as the benchmark and the weight that is measured later as the variation amount. Then, the regression analysis processing unit acquires the approximate straight line based on the weight variation amount of the measurement element, which is acquired by the variation amount acquisition unit, and in addition, the data including the variation amount per an hour and the time needed to reach the expected variation amount are acquired based on the approximate straight line. Then, the measurement result of the acquired weight variation due to the physical exercise of the measurement subject and the data (letter data and a graph and so forth) of the processed result are subjected to the processing with the image processing unit, and displayed on the display element.

In addition, approximately 10 minutes is not necessary to be strictly 10 minutes, and it is not issue that the time can be more or less such minutes and the measurement can be skipped (missed), in addition, the number of measurement in between runnings is not limited to two and, for example, just once after 15 minutes pass is affordable, in addition, the measurement is mandatory in between runnings. Specifically, at least twice measurements with some time interval meet the requirement between the beginning and the end of the total 30 minutes running. In addition, the weight measurement can be carried out every after running the constant distance whereby the weight measurement can be carried out based on the other criteria than the elapsed time.

In addition, the variation measurement device for physical activity can measure the difference (weight variation amount) of the body weight of the measurement subject before and after a meal. Specifically, conventionally, the calorie intake is estimated from the meal content, of which photo is sent to estimate (calculate) thereby whereby the actual weight variation amount is acquired so that the weight variation is qualitatively realized. On the other hand, the weight measurement element acquires the actual weight data of the measurement subject before and after the meal, so that the effect of the meal on the weight can be quantitatively realized. Accordingly, the measurement subject can manage the variation amount of the weight data due to the meal in addition thereto using the variation measurement device for physical activity. In addition, referring, to FIG. 2, the weight variation due to the meal and the elimination (urination) and so forth can be inclusively measured.

In addition, according to the aspect of the present Embodiment, the variation measurement device for physical activity can be owned by the user in the own home (as a personal property) and subjected to use, or can be installed permanently in a working-place, a fitness club, a restaurant, a sports gym, and a hospital and so forth to be used. In addition, the weights and so forth (weights, weight data, regression analysis results) that are measured between a plurality of variation measurement devices for physical activity (or devices capable of implementing the variation display method for physical activity) installed in the different locations can be exchanged, and the weights and so forth (weights, weight data, regression analysis results) that the same measurement subject measures in the different locations (devices) can be collectively processed and displayed.

In addition, according to the aspect of the Embodiment set forth above, the example (referring to FIG. 1), in which the measurement subject who stands on the weight measurement element with both feet, is illustrated, but the present invention is not limited thereto. According to the aspect of the present Embodiment of the present invention, the measurement subject who stands on the weight measurement element with one foot can measure the weight. Accordingly, the size of the weight measurement element can be minimized to trim the weight and be easily portable and carriable.

In addition, according to the aspect of the Embodiment set forth above, the example in which the weight measurement element is included in the variation measurement device for physical activity is illustrated, but the present invention is not limited thereto. According to the aspect of the present invention, the weight measurement element may not comprise the variation measurement device for physical activity. Specifically, the weight data can be obtained in communication with the device that measures the weight of the measurement subject, which is installed separately from the variation measurement device for physical activity, or the user per se directly inputs the measurement result of the weight of the measurement subject into the variation measurement device for physical activity so that the weight data can be acquired.

In addition, according to the aspect of the Embodiment set forth above, the example in which the weight measurement element measures the weight in the unit of 10 g, but the present invention is not limited thereto. According to the aspect of the present invention, the weight unit that the weight measurement element uses in the measurement is satisfactory as long as the accuracy level is attained at which the weight variation of the measurement subject due to one predetermined daily activity is measurable. In addition, the unit larger than 10 g, e.g., 20 g and 50 g, or the unit smaller than 10 g, e.g., 1 g and 5 g, that are relatively smaller units (e.g., a unit smaller than 100 g) can be applied.

In addition, according to the aspect of the Embodiment set forth above, the example in which when the variation amount of the weight data per an hour is displayed, the time unit is each 1 minute or 10 minutes, but the present invention is not limited thereto. According to the aspect of the present Embodiment, the time unit can be arbitrarily (e.g., every hour) applied when the variation amount of the weight data per an hour is displayed. In addition, the user can select and input the time unit to be displayed.

In addition, according to the aspect of the Embodiment set forth above, the example, in which the time when the variation amount of the weight data reaches the expected variation amount is displayed, the expected variation amount is 100 g, is illustrated, but the present invention is not limited thereto. According to the aspect of the present invention, the expected variation amount can be arbitrary amount (e.g., 1 Kg). In addition, the user can select and input the expected variation amount.

In addition, according to the aspect of the Embodiment set forth above, the example, in which when the weight variation amount is acquired, the benchmark is the first measured weight, is illustrated, but the present invention is not limited thereto. According to the aspect of the present invention, for example, the last weight measured at the end of the physical activity and so forth, which is the weight other than the first measured weight, can be applied to the benchmark.

In addition, according to the aspect of the Embodiments set forth above, the example, in which the variation amount of the weight data is subjected to fit the approximate straight line using the regression analysis, but the present invention is not limited thereto. According to the aspect of the present invention, the variation amount of the weight data can be subjected to fit the approximate curve using the regression analysis. For example, when the weight decrease rate increases (or decreases) gradually along the ongoing physical exercise, the fitting using the approximate curve is more appropriate. In addition, the approximate curve is a curve based on an elementary function including an exponent function, a logarithm function, and an idempotent function and so forth, and a combination thereof.

In addition, according to the aspect of the Embodiment as set forth above, for example, each of the display element, the memory element and the control element is installed separately from the weight measurement element, but the present invention is not limited thereto. According to the aspect of the present invention, some (or all) of the display element, the memory element and the control element can be formed with the weight measurement element in a unified manner. In addition, the image processing unit of the control element can be a separate hardware from the main body of the control element.

In addition, according to the aspect of the Embodiment set forth above, for example, the display element displays the measurement results using the variation measurement device for physical activity and the data of processed results (the variation amount and the graph based on the variation amount and so forth), but the present invention is not limited thereto. According to the aspect of the present invention, in addition to the display on the display element, the measurement results and the data of the processed results can be output to a smartphone, a tablet terminal, and a PC (personal computer) and so forth that are owned by the user so that the user can browse the measurement results and the data of the processed result using the own smartphone, the own tablet terminal, and the own PC, and so forth.

In addition, according to the aspect of the Embodiment as set forth above, for example, each of the control element and the display element is installed to the PC and so forth connected to the weight measurement element, but the present invention is not limited thereto. According to the aspect of the present invention, the measurement subject can download and so forth to install the software capable of executing the method of displaying the variation amount for physical activity to the own smartphone, tablet and PC and so forth, and execute such software (application) so that the user own smartphone, table terminal and PC and so forth can be operative as the control element and the display element of the variation measurement device. In such case, for example, the data relative to the weight of the measurement subject, which are measured using the weight measurement element, are output to the smartphone, the tablet terminal, and the PC and so forth that are owned by the user, the weight data input to the smartphone, the tablet terminal, and the PC and so forth that are owned by the user are processed, and the processed results can be displayed on the display element such as the smartphone, the tablet terminal, and the PC, and so forth.

As an example, the weight measurement element and the control element without the image processing unit are installed in the housing by which the measurement subject measures body-weight and the image processing unit and the display element can be installed to the smartphone and so forth. At this time, when the measurement subject gets on, the measurement element (the measurement plate and so forth of the weight measurement element) to measure the weight of the measurement subject, the weight of the measurement subject is measured, and then the processings from an acquisition of the weight data, to a date processing (calculation) of such as regression analysis and so forth are executed by the control element (control element without the image processing unit) in the housing. Next, the data of the processing results are sent to the smartphone and so forth, the image processing corresponding to the screen size of the smartphone and so forth is executed by the image processing unit (data processing unit such as CPU and so forth), and the graph of the weight variation amount and the weight variation amount every hour and so forth are displayed on the display element of the smartphone.

In addition, according to the aspect of the Embodiments set forth above, for example, the variation display method for physical activity is applied to the variation measurement device that displays the variation amount of the weight data of the measurement subject, but the present invention is not limited thereto. According to the aspect of the present invention, the variation display method for physical activity displays the variation amount of the weight data, and in addition, can be applied to the activity amount measurement device that displays comprehensively the numeral data relative to the body, including the calorie consumption of the measurement subject, an amount (index) of body fat, a removed fat amount, a heart rate, a depth of sleep and so forth.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will, be understood by those of skill in the art as also being identified as or capable of operating the systems and devices and subcomponents noted herein and structures that accomplish the functions without restrictive language or label requirements since those of skill in the art are well versed in related variation measurement devices and display methods, arts, devices, computer and operational controls and technologies of measurement and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that, the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, elements, features, and/or steps have been described above generally in terms of their functionality and inter-relatability. Whether such functionality is implemented as hardware or software depends upon the particular application and design constraints imposed on the overall system. Skilled computer artisans (engineers, programmers, scientists etc.) may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC) a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the PAD™ and Android™ platform tablet, and all other kinds of computers and computing platforms.

A processor may also be implemented as a combination of computing devices, e.g., a combination of a DSP and a processor (or microprocessor), a plurality of processors/microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory. Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can, comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Having described at least one of the preferred embodiments of the present in with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A variation measurement device for a physical activity, comprising:
    a weight measurement element that acquires weight data for each of a plurality of measurement times during a single weighing session;
    a weight data memory element that stores in a weight data memory said weight data acquired by the weight measurement element over time;
    a control element that calculates a variation amount, which is a difference between a benchmark weight data that is said weight data at one of the plurality of measurement times and other weight data;
    a display element that displays said variation amount over time that varies depending on a predetermined physical activity;
    wherein the display element is configured to display an approximate curve or an approximate straight line fitted the variation amount from the benchmark weight to the approximate straight line or the approximate curve by regression analysis;
    wherein the display element is configured to display a plurality of curves comprising the approximate curve obtained on a plurality of days of the same subject, or a plurality of straight line comprising the approximate straight line obtained on a plurality of days of the same subject, or a plurality of curves comprising the approximate curve obtained on a plurality of different subjects, or a plurality of straight lines comprising the approximate straight line obtained on a plurality of different subjects, and
    the plurality of straight lines and the plurality of curves have the same height of a starting point to indicate the benchmark weight data.

2. The variation measurement device for physical activity, according to claim 1, wherein:
    said display element displays said variation amount based on a decreasing amount of a measured weight between the beginning and the end of said predetermined physical activity.

3. The variation measurement device for physical activity, according to claim 1, wherein:
    said control element fits said variation amounts from said benchmark to at least one of an approximate straight line and an approximate curve by a regression analysis, and displays a graph denoting a time-course variation of a plurality of said weight data based on at least one of said approximate straight line and said approximate curve that are acquired by said display element.

4. The variation measurement device for physical activity, according to claim 3, wherein:
    said control element estimates a time period in which said variation amount of said weight data attains an expected variation amount based on at least one of said approximate straight line and said approximate curve acquired by said fitting, and displays said time period on said display element.

5. The variation measurement device for a physical activity, according to claim 3, wherein:
    said control element displays said variation amount of said weight data, that is converted to per a unit time, on said display element based on at least one of said approximate straight line and said approximate curve acquired by said fitting.

6. A display method of a variation for a physical activity, comprising:
    a step of measuring a weight of a measurement subject multiple times during a single weighing session between a beginning of a predetermined physical activity of a measurement subject and an end of said predetermined physical activity;
    a step of storing weight data of each of said weight that is measured multiple times in association with each measurement time;
    a step of acquiring variation amount of said weight data, that is a difference between benchmark weight data that is specified among said weight data that are stored and said weight data other than said benchmark weight data;

a step of displaying said variation amounts that vary depending on said predetermined physical activity, wherein said variation amount is acquired based on said benchmark weight of said weight data of said measurement subject;

wherein the step of displaying said variation amounts that vary depending on said predetermined physical activity includes a step of displaying an approximate curve or an approximate straight line fitted the variation amount from the benchmark weight to the approximate straight line or the approximate curve by regression analysis;

wherein the step of displaying said variation amounts that vary depending on said predetermined physical activity includes a step of displaying a plurality of curves consisting of the approximate curve obtained on a plurality of days of the same subject, or a plurality of straight line consisting of the approximate straight line obtained on a plurality of days of the same subject, or a plurality of curves consisting of the approximate curve obtained on a plurality of different subjects, or a plurality of straight lines consisting of the approximate straight line obtained on a plurality of different subjects; and the plurality of straight lines and the plurality of curves have a same height of starting point to indicate the benchmark weight data.

7. The display method of said variation for said physical activity, according to claim 6, wherein:

the step of displaying said variation amount of the weight based on a decrease amount of a measured weight between the beginning and the end of the physical activity.

8. The variation measurement device for a physical activity, according to claim 1, wherein:

the display element is configured to display a rate of change in weight fluctuation obtained from the approximate straight line or the approximate curve.

9. The variation measurement device for a physical activity, according to claim 1, wherein:

wherein the display element that displays said variation amount per hour or per minute that varies depending on a predetermined physical activity.

10. The variation measurement device for a physical activity, according to claim 1, wherein:

the control element that calculates a variation amount with a predetermined value of less than 100 g as the unit, which is a difference between a benchmark weight data that is said weight data at one of the plurality of measurement times and other weight data; and the display element that displays said variation amount with a predetermined value of less than 100 g as the unit over time that varies depending on the predetermined physical activity; and wherein the display element is configured to display an approximate curve or an approximate straight line fitted the variation amount with a predetermined value of less than 100 g as the unit from the benchmark weight to the approximate straight line or the approximate curve by regression analysis, and display a rate of change in weight fluctuation obtained from the approximate straight line or the approximate curve.

* * * * *